US012702532B2

(12) United States Patent
White et al.

(10) Patent No.: US 12,702,532 B2
(45) Date of Patent: Aug. 11, 2026

(54) SYSTEMS AND METHODS FOR PRODUCING A CONTROLLED OPERATING ENVIRONMENT

(71) Applicant: CLAEROSOL LLC, Miramar, FL (US)

(72) Inventors: Daniel T. White, Gainesville, FL (US); Eamonn P Fitzgerald, Miramar, FL (US)

( * ) Notice: Subject to any disclaimer, the term of this patent is extended or adjusted under 35 U.S.C. 154(b) by 162 days.

(21) Appl. No.: 18/285,651

(22) PCT Filed: Apr. 4, 2022

(86) PCT No.: PCT/US2022/023373

§ 371 (c)(1),
(2) Date: Oct. 4, 2023

(87) PCT Pub. No.: WO2022/216636

PCT Pub. Date: Oct. 13, 2022

(65) Prior Publication Data

US 2024/0189083 A1 Jun. 13, 2024

Related U.S. Application Data

(60) Provisional application No. 63/210,902, filed on Jun. 15, 2021, provisional application No. 63/171,057, filed on Apr. 5, 2021.

(51) Int. Cl.

| | |
|---|---|
| ***A61C 17/06*** | (2006.01) |
| ***A61L 9/20*** | (2006.01) |
| ***B01D 46/00*** | (2022.01) |

(52) U.S. Cl.

CPC .......... *A61C 17/096* (2019.05); *A61C 17/065* (2019.05); *A61L 9/20* (2013.01);

(Continued)

(58) Field of Classification Search

CPC ... A61B 90/05; A61B 90/40; A61B 2090/401; B08B 15/00; A61G 13/108;

(Continued)

(56) References Cited

U.S. PATENT DOCUMENTS 3,537,447 A * 11/1970 Gauthier ................ A61G 15/14 433/29
3,877,691 A * 4/1975 Foster ................. A61M 16/009 128/200.24

(Continued)

*Primary Examiner* — Heidi M Eide
*Assistant Examiner* — Shannel Nicole Belk
(74) *Attorney, Agent, or Firm* — Donald K. Jones

(57) ABSTRACT

An air handling and filtration/treatment system (whether portable of affixed) for the mitigation and management of airborne biological contaminants (either those pre-existing or those that may become generated) that includes a suspended air in-take assembly containing a removable filter; that includes a deflector having ducting leading to a housing assembly that includes a UV sanitizer, a fan assembly and controller; and includes an outflow assembly that includes ducting leading to a position able manifold having a plurality orifices. The manifold and deflector are laterally offset from the housing assembly and vertically aligned with each other. The manifold is positioned to encircle the bioaerosol source. When the system is operated, the fan assembly suctions air through the filter positioned at the duct inlet, through the UV sanitizer, and expels the treated air through the manifold orifices which are directed towards the deflector to create an air curtain and negative pressure environment which contains the newly generated bioaerosols directing them to the filter of the in-take assembly.

18 Claims, 6 Drawing Sheets

(52) U.S. Cl.
CPC ..... *B01D 46/0028* (2013.01); *B01D 46/0049* (2013.01); *A61L 2209/12* (2013.01); *A61L 2209/14* (2013.01); *B01D 2273/30* (2013.01); *B01D 2279/65* (2013.01)

(58) Field of Classification Search
CPC ... A61C 19/007; A61C 17/096; A61C 17/065; A61C 17/06; A61C 17/08; Y10S 128/917
See application file for complete search history.

(56) References Cited

U.S. PATENT DOCUMENTS

| | | | | |
|---|---|---|---|---|
| 4,140,105 | A * | 2/1979 | Duvlis | A61G 13/108 454/191 |
| 8,465,576 | B2 * | 6/2013 | Della Valle | A61G 13/108 55/467 |
| 2010/0081368 | A1 * | 4/2010 | Della Valle | A61G 13/108 454/228 |
| 2021/0331109 | A1 * | 10/2021 | Sahiholnasab | B01D 46/0041 |
| 2024/0189083 | A1 * | 6/2024 | White | A61L 9/20 |

* cited by examiner

FIG. 6

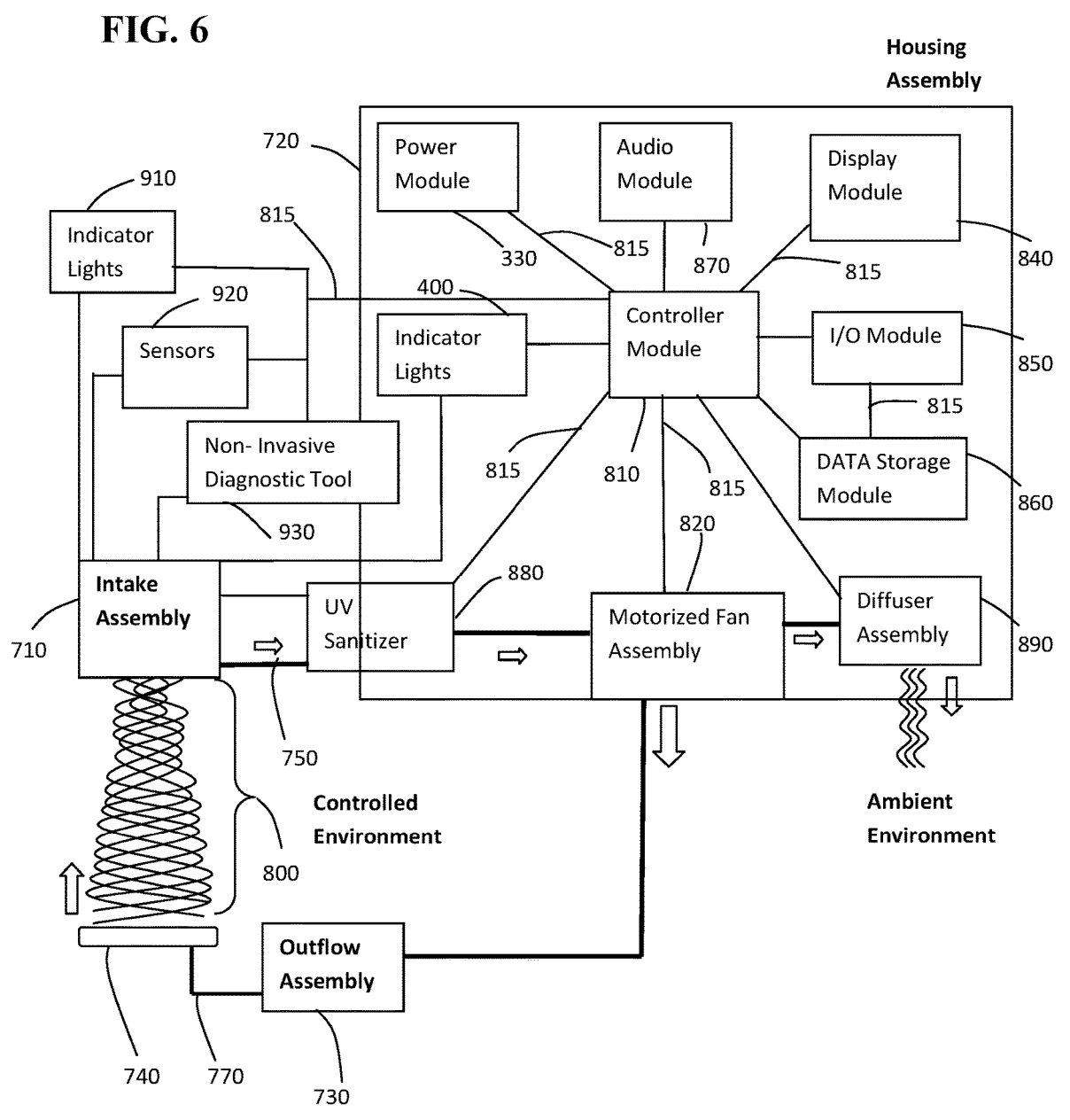

Housing Assembly
720
Power Module
Audio Module
Display Module
910
Indicator Lights
815
330
815
870
815
840
920
400
Sensors
Indicator Lights
Controller Module
I/O Module
850
815
Non- Invasive Diagnostic Tool
815
810
815
DATA Storage Module
860
930
820
880
Intake Assembly
UV Sanitizer
Motorized Fan Assembly
Diffuser Assembly
890
710
750
Controlled Environment
Ambient Environment
800
Outflow Assembly
740
770
730

SYSTEMS AND METHODS FOR PRODUCING A CONTROLLED OPERATING ENVIRONMENT

BACKGROUND

1. Field of the Invention

The present disclosure relates to an air handling and filtration/treatment system and methods. More particularly, the disclosure relates to an area-specific or an area-directed air handling and filtration/treatment system (whether portable of affixed) that produces a negative-pressure environment to mitigate and otherwise manage airborne biological contaminants (either those pre-existing or those that may become generated) during a physically-close encounter involving one or more persons with a given, potential pathogenic vector (who may be another person or an animal), which can be best exemplified for use in the conduct and ordinary-course of dental and oral surgical procedures.

2. State of the Art

Providing healthcare involves close physical proximity to patients, who may be infected with contagious pathogens. These pathogens may take the form of bioaerosols produced merely by normal respiration, notwithstanding any interventional procedure. The human respiratory system produces particles through generation mechanisms (i.e., breathing). Exhaled particles range in diameter from 0.01 and 1000 μm depending on the particular mechanism (coughing, sneezing, talking, etc.) and site of origin. These droplets are formed through atomization process of respiratory fluids (sputum/saliva), having a wide range of viral load (102 to 1011) copies/mL. During deep expirations within the lungs, small airways close and the reopening process produces minute particles. When exhaled, these particles have a diameter of <4 μm. These consist of sub-micron droplets directly emitted from respiratory activities and the droplet nuclei formed from the evaporation of super-micron droplets may contain viruses of size (0.02-0.3) μm. Studies have shown that the production rate between individuals vary widely. One study measured aerosol concentrations among individuals and found concentrations levels between a few tens of particles per liter of exhaled air to several thousand particles per liter. Other studies have consistently found that a significant portion (42-63%) of droplets containing virus causing influenza are in the respirable size range.

Bioaerosols are generally considered extremely small airborne particles comprised of, or containing viruses, bacteria, viral parts (i.e., RNA), proteins, pollens, dander, fungi, or fungal spores. Bioaerosols are generally defined as having a diameter of less than about 5 microns, and can remain suspended in air for many hours at infectious concentration levels, especially in indoor areas having poor ventilation. The protracted airborne suspension time for these bioaerosols given their structure, and small size, and weight, can pose a substantial infectious pathogen transmission risk to those coming in contact with them, either directly through inhalation or contact with other exposed mucus membranes or indirectly through surface contact, even if the exposed persons were not physically present in the operatory at the time of contaminant generation.

Despite the recent increases in telemedicine during the COVID-19 pandemic, most healthcare examinations and procedures are still conducted in person, within an office-suite setting containing multiple rooms or operatories. The HVAC systems of many of these offices are not equipped for patient-isolation procedures used by hospitals in the case of infectious pathogens. In many dental offices, for example, rooms traditionally may even contain more than one chair (e.g., operatory) with multiple patients having procedures done simultaneously, while in rather close physical proximity to one another.

In particular, dentists, oral surgeons, dental hygienists, and their assistants (e.g., dental professionals) are routinely exposed to heightened risk from bioaerosols due to the inherent nature of the practice of dentistry. Dental professionals' common, interventional encounters with patients involve a wide variety of procedures ranging from simple cleanings, fillings and tooth extractions to root canals, gum grafts, tooth implants and maxillofacial reconstructive surgery. In each case, the patient's head (nose, mouth, eyes, and each of their respective fluids), skin, hair, exhalation, and clothing—each of which may be a potential source or pathway of contagions—become inextricably introduced in some unavoidable way within the operatory field, and close to the attending dental professionals. Also, with regard to dentistry in particular, procedures often involve not only the dental professionals' close, prolonged, physical proximity to patients, but also the frequent use of high-speed handpieces and ultrasonic scalars capable of aerosolizing a patient's saliva and blood, which combine to present another heightened transmission risk of aerosolized pathogens. Moreover, the use of water-cooled, rotating, or vibrating instrumentation within the oral cavity combined with a patient's normal respiration, talking, laughing, coughing, or sneezing also creates additional bioaerosols and other larger droplets (a/k/a spatter or splatter), which can contain blood and saliva-based pathogens of the patient. These larger droplets do not remain suspended in air very long due to their size and weight and settle out rather quickly on immediately surrounding surfaces. However, when dehydrated, they become lighter (and known as droplet nuclei) and can become bioaerosols. While dental professionals performing the procedures wear traditional personal protective equipment (PPE) (typically involving disposable gloves, eyewear, face masks and face shields), there is still a potential risk of contamination and transmission due to patient-generated spatter and other biological materials that become attached to the PPE and/or become aerosolized or airborne (e.g., bioaerosols) during and after the procedure, in some instances simply due to a patient's normal respiration, talking, laughing, coughing, or sneezing.

These bioaerosols may infect not only the immediate service providers through some mode of transmission (contact or inhalation) notwithstanding their PPE, but they have been shown to travel long distances and remain aloft in confined spaces for protracted periods of time thereby posing inhalation risks to other office staff and patients notwithstanding the office's existing heating/ventilation/air conditioning (HVAC) systems. In hospital settings, research has shown the ability of bioaerosols to travel outside of patient-isolation rooms and arrive in the ambient air of, or surfaces located in, other areas of buildings. As a consequence, patients may become potentially exposed to the remnant bioaerosols created by other patients in other office areas or past patients in the same area, as well as the bioaerosols originated by normal respiration, coughing, and sneezing of healthcare professionals that escape into the local atmosphere notwithstanding their use of PPE or sanitary procedures.

There is a need for a system that can provide an enhanced level of protection to patients and providers through better mitigation in the form of non-invasive, integrated system of managing, mitigating and/or remediating (which may include, without limitation, the containing, capturing, identification, isolating, blocking, re-directing, diluting, treating and/or evacuating) of bioaerosols during and after dental or other health care screening procedures to reduce the exposure and/or transmission risk of infectious pathogens to patients, visitors, dental and other healthcare professionals and their administrative staff, that does not otherwise unduly interfere with or disrupt the necessary procedures, routines and proximity of the patient and his or her healthcare providers, such as dental professionals.

SUMMARY

There is provided an area-specific or area-directed (portable, affixable or removable) air handling and treatment system for the mitigation, management and/or remediation (including, without limitation, the containment, capture, isolation, blocking, re-direction, dilution, treatment, and/or evacuation during and after dental examinations and procedures) of bioaerosols (patient generated or otherwise) within the operatory theatre that includes an air in-take assembly, a housing assembly and an outflow assembly including a mechanism to create an air shield or curtain. The air in-take assembly has a deflector that is connected to and suspended by a movable boom arm that contains an air duct having a first end positioned through the deflector and coupled to a removable filter. The second ends of the duct and boom arm are coupled to the housing assembly. The boom arm and duct of the in-take assembly can be telescoping to aid in positioning the deflector. The housing assembly includes a motorized fan assembly, a user interface, controller, and power supply. The second end of the in-take assembly duct is in fluid communication with the in-flow to the fan assembly. The outflow assembly includes a duct having a first end coupled to the housing assembly in fluid communication with the out flow from the fan assembly and a second end coupled to a manifold having a plurality of orifices positioned around its periphery. The deflector of the in-take assembly is positioned vertically above and generally aligned with the manifold such that the plurality of orifices in the manifold is directed towards the deflector. The manifold is adapted to be positioned entirely or partially around (whether sitting at, above, or below) the head of a patient, some other body part or area, or his or her entire body. When the system is operating, the motorized fan assembly suctions air through the removable filter towards the fan assembly and expels the treated air through the outflow assembly where the plurality of orifices in the manifold directs the treated air towards the deflector. The directed air from the manifold orifices generates an air curtain (or shield) creating a negative pressure environment by creating an upward flow of air around the head or body of the patient in which any bioaerosols (including droplet nuclei) expelled by the patient or generated during a procedure are substantially contained and diluted within the bounds of the air curtain and directed towards the removable filter of the in-take assembly for further processing. The airflow speed is preferably between 2 and 12 miles per hour. Additionally, the airflow is preferably laminar. The system also captures bioaerosols that may be situated or generated (i.e., directly by the healthcare providers or indirectly through operation of human plumes) outside the air curtain, continuously scrubbing the ambient air of the operatory.

The deflector has a geometry which is generally planar (although it may be arcuate) and a shape that is preferably rectangular or oval although other shapes may be suitable. The deflector aids in maximizing airflow to the removable filter from the manifold while minimizing non-targeted (i.e., room air vertical to the deflector) from reaching the removable filter. The deflector is preferably transparent as not to interfere with overhead lighting, lightweight, and durable. Suitable plastics include Polyethylene terephthalate (PET), Polycarbonate (PC) polyvinyls, acrylics, polystyrenes, copolymers and blends.

There is provided a manifold that can be situated on, above or beneath the patient (and surrounding the patient or a targeted portion of the patient partially or entirely) and that in dental applications, for example, takes the form of a bib or pillow-type feature resting on the dental chair and/or patient, in each instance surrounding all or a portion of the patient's face. In its exemplary embodiment in dental and applications, this bib is generally planar and has a rectangular (with rounded corners) or oval shape similar to that of the deflector and sits on, or slightly above or beneath, the patient's head or body. The bib is generally constructed to have a non-permeable membrane with a cut out for a patient's head and an outer periphery that contains the plurality of orifices. The outer periphery of the bib may be inflatable. While the bib may be reusable it is preferably lightweight, flexible, and disposable.

In accordance with an embodiment the replaceable filter includes an air filtration media, such as an ULPA or HEPA filter. A high-efficiency particulate air or HEPA filter is generally defined by various standard bodies as one that provides up to 99.97% efficiency on particles down to 0.3 microns in size. Ultra low particulate air or ULPA filters, which have an efficiency of up to 99.9995% on particles as small as 0.12 microns.

To improve the air treatment there is provided an in-take assembly and or housing assembly that acts as a transient air dwell that can include chemical, biological or other physical or electric treatments of the evacuated air, such as an ultra violet (UV) light or sanitizer. Preferably the UV sanitizer takes the form of a UVC lamp. However, more preferably the UV sanitizer takes the form of an array of UVC light emitting diodes (LED) located in the in-take assembly. The UVC LEDs may be positioned in the in-take assembly to sanitize the internal surfaces of the in-take assembly components in addition to surrounding airflow. While the UVC LEDs may be positioned in the in-take assembly they may also be positioned in the housing assembly and controlled by the controller There is provided an air handling system that includes a diffuser in or attachable to the housing assembly. The diffuser permits all or a portion of the treated air expelled by the fan assembly to be (1) introduced directly into the ambient air at a reduced speed, (2) recycled for use with the patient, or (3) evacuated to another location (i.e., outside or to the office's HVAC system).

There is provided an air handling and filtration/treatment system that includes a non-invasive diagnostic tool, which may allow for a real-time diagnosis or rapid detection and identification of bioaerosol contaminates, including pathogens or pathogen families. The diagnostic tool may incorporate or utilize biosensors, materials or reagents that change properties (e.g. color, shape, electrical, etc.) in the presence of pathogens, spectroscopy or microscopy to aid in contaminate detection and or identification.

There is provided a method of monitoring bioaerosols from members of a population that includes the steps of:

- providing an air handling and treatment system as described above;

positioning the manifold appropriately about a patient;

operating the air handling and treatment system such that bioaerosols emanating from the patient are directed towards the filter via the airflow generated from the manifold and captured within the filtration medium of the filter;

removing the filter (including the filtration medium) from the air handling and treatment system;

positioning a sealable barrier about the filter and or filter media;

sealing said sealable barrier such that the filter and or filter media is not exposed to the ambient environment;

labeling the sealed filter with information that corresponds to procedural data that may include any of the following: patient ID, date, airflow settings, procedure type, procedure duration, time of procedure, temperature or humidity alone or in combination; and sending the sealed filter to a location for captured bioaerosol analysis.

BRIEF DESCRIPTION OF THE DRAWINGS

FIG. 6 is a schematic of the system's hood showing an example of how the system may be used as a real-time detection system by attaching one or more mechanical sensors to the underside of the hood that alert the immediate audience of the presence of one or more pathogens.

DETAILED DESCRIPTION

Figure 1:
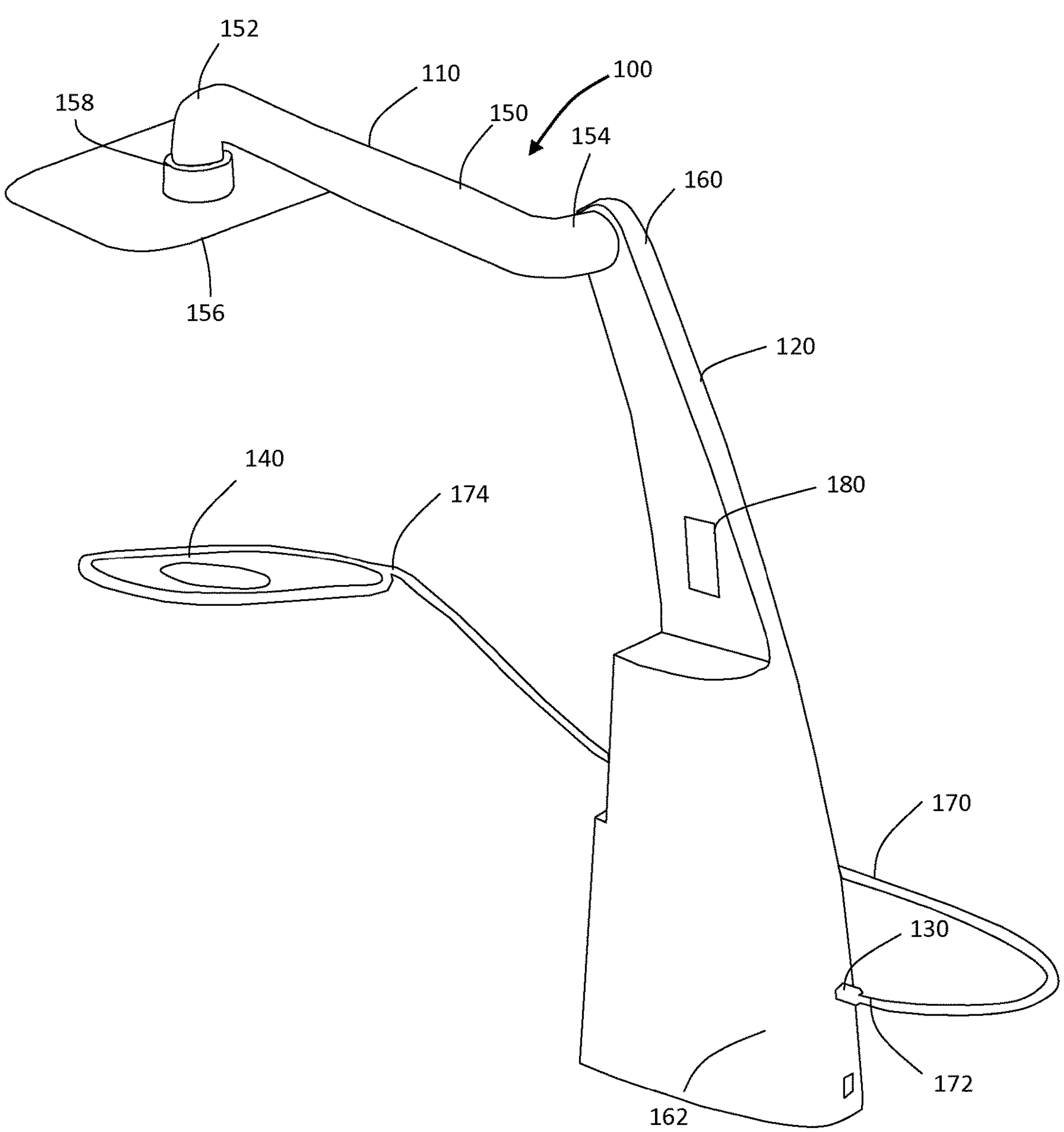
FIG. 1 is a perspective view of an air handling system.

FIG. 1 shows a portable air handling and filtration/treatment system 100 for use in mitigating and otherwise managing bioaerosols generated during dental procedures. The system includes an in-take assembly 110, a housing assembly 120, and an outflow assembly 130 coupled to a bib 140. The air in-take assembly 110 includes a boom arm air duct 150 having a first end portion 152 and a second end 154 portion. The second end portion 154 of the boom air duct is connected to housing assembly 120 while the first end portion 152 is connected to an air deflector 156 and a removable filter 158. The housing assembly 120 has an upper portion 160 that extends to a spaced apart lower portion 162 and typically contains a number components or modules such as, internal ducts, a motorized fan assembly, a user interface, controller, and power supply. The second end portion 154 of the in-take assembly air duct 150 couple to the upper portion 160 of housing assembly 120 and is in fluid communication with the in-flow duct(s) that lead to the internal fan assembly. The outflow assembly 130 includes a flexible duct 170 duct having a first end 172 coupled to the housing assembly lower portion 162 that is in fluid communication with the out flow from the fan assembly and a second end 174 coupled to bib 140. Bib 140 is the portion of the air handling filtration and treatment system that most likely to be patient contacting. The operation of the system is generally accessed via the user interface 180 which provides visual & audio feedback, data management (communication, transmission and storage) and programming capabilities as a part of the housing assembly.

Figure 2:
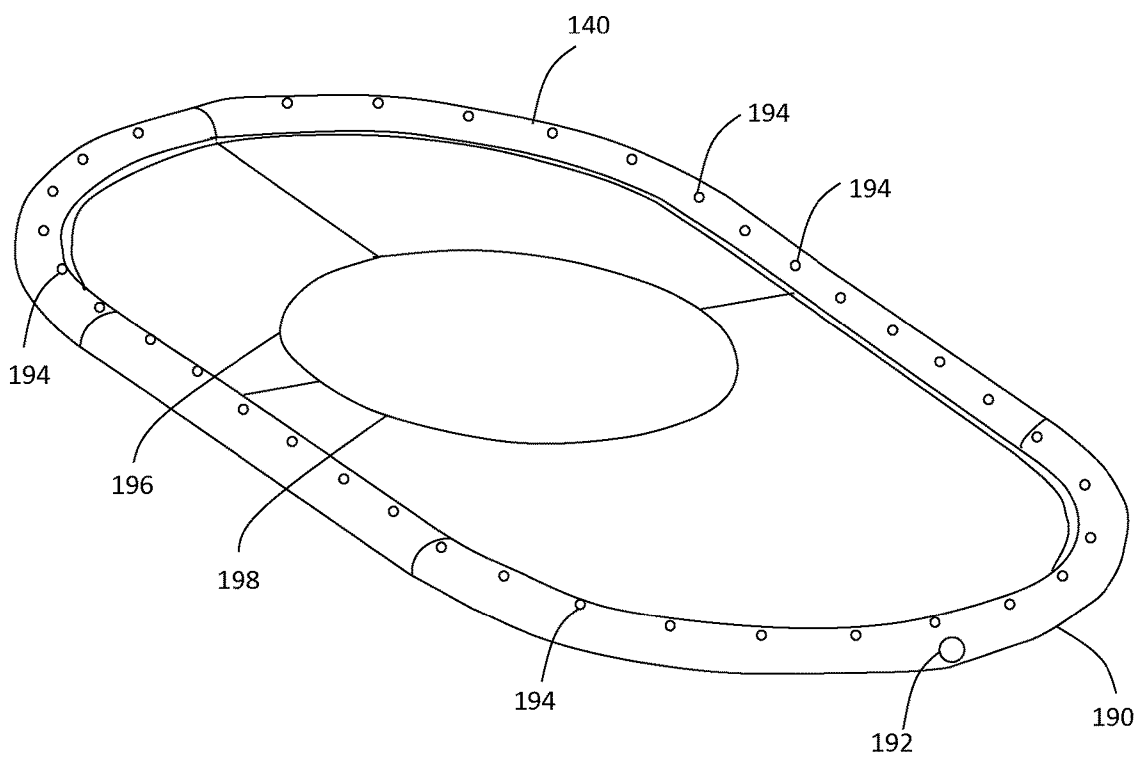
FIG. 2 is an enlarged perspective view of the bib member of the air handling system shown in FIG. 1.

FIG. 2 shows an enlarged view of the bib 140. The bib 140 is generally light weight, flexible and adapted to be positioned around the head of a patient. The general shape of the bib is ovoid, however, other shapes may be suitable for use. The outer periphery or primary tube 190 of the bib is connected to second end 174 of flexible duct 170 at air flow inlet 192. Primary tube 190 includes a plurality of orifices 194 along the length of the tube such that air flow from the fan assembly through duct 170 exits from the plurality of orifices 194 positioned along the length of primary tube 190. The interior of bib 140 preferably takes the form of a sheet or membrane 196 connected to and being bordered by primary tube 190. Membrane 196 preferably is formed from non-permeable material and includes opening 198 for fitting about the head of a patient. As can be appreciated bib 190 may be formed of disposable thin film materials having appropriately positioned orifices such that when air flow enters inlet 192, primary tube 190 inflates.

Figure 3A:
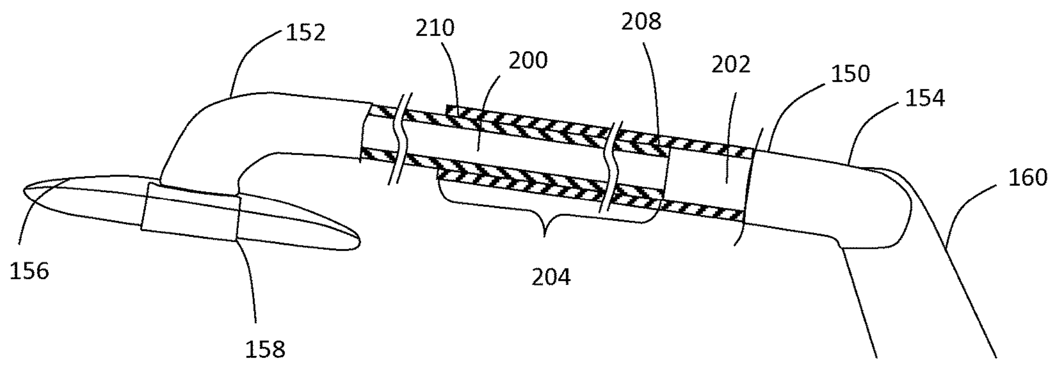
FIGS. 3A and 3B are enlarged side views of the in-take assembly of the air handling system showing the telescopic extension of the boom arm.
Figure 3B:
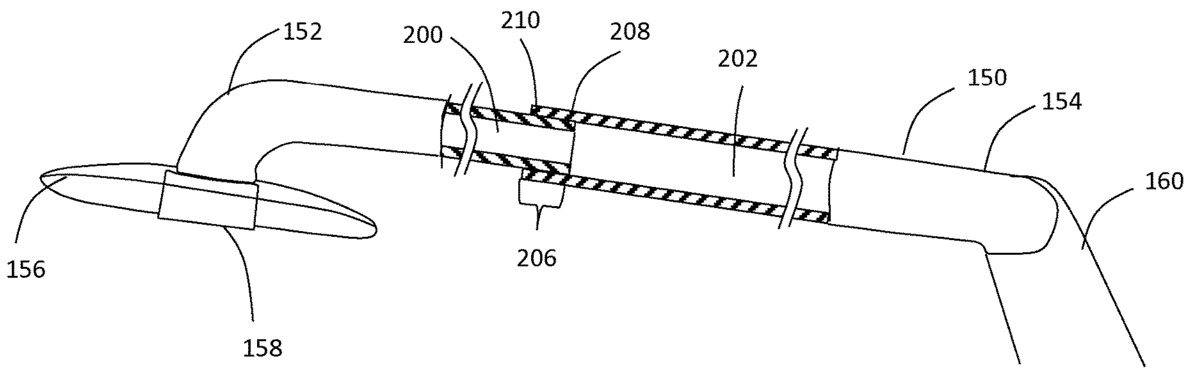

When preparing to use the air handling and filtration treatment system, the bib 140 is placed on a patient and the deflector 156 of the in-take assembly is positioned vertically above and generally aligned with the bib 140 such that the plurality of orifices 194 in the bib is directed towards the deflector. To properly align the deflector with the bib, air duct 150 of the in-take assembly 110 may be telescoping and adjusted as shown in FIGS. 3A and 3B. First end portion 152 is telescopically positioned within second end portion 154 (the walls of each end portion overlap) such that lumen 200 of first end portion 152 is in fluid communication with the lumen 202 of second end portion 154. Duct 150 has a contracted configuration as shown in FIG. 3A having a first overlap distance 204 and an extended configuration shown in FIG. 3B having a second overlap distance 206. As can be appreciated when duct 150 is in the contracted configuration the magnitude of the first overlap distance 204 is greater than the magnitude of the second overlap distance 206 when duct 150 is in the extended configuration. The length of duct 150 in telescoping form is adjustable and to insure that manipulation of the length does not allow the introduction of foreign material the telescoping portions may include wiper seals 208 and 210. When the system is operated in its operative mode for examinations or procedures, the motorized fan assembly suctions air through the removable filter 158 towards the fan assembly and expels the filtered or treated air, in part, through the outflow assembly 130 where the plurality of orifices 194 in the bib directs that portion of the treated air back towards the deflector 156, and the remainder of the treated air is expelled elsewhere. The directed air from the bib orifices generates an air curtain creating a negative pressure environment around the head of the patient in which any bioaerosols expelled by the patient or generated during a procedure are contained within the bounds of the air curtain, diluted, and directed towards the removable filter of the in-take assembly. While a substantial portion of the out flow of treated air from the fan assembly is directed to the bib (which acts like a manifold), a portion of the treated air may be directed directly into the operatory environment, into the operatory's HVAC system, or directed to be expelled at some other terminal outlet. During its "room turn" operable mode, the system can direct some or all of the treated air into the local operatory environment, into the operatory's HVAC system, or directed to be expelled at some other terminal outlet.

Figure 4:
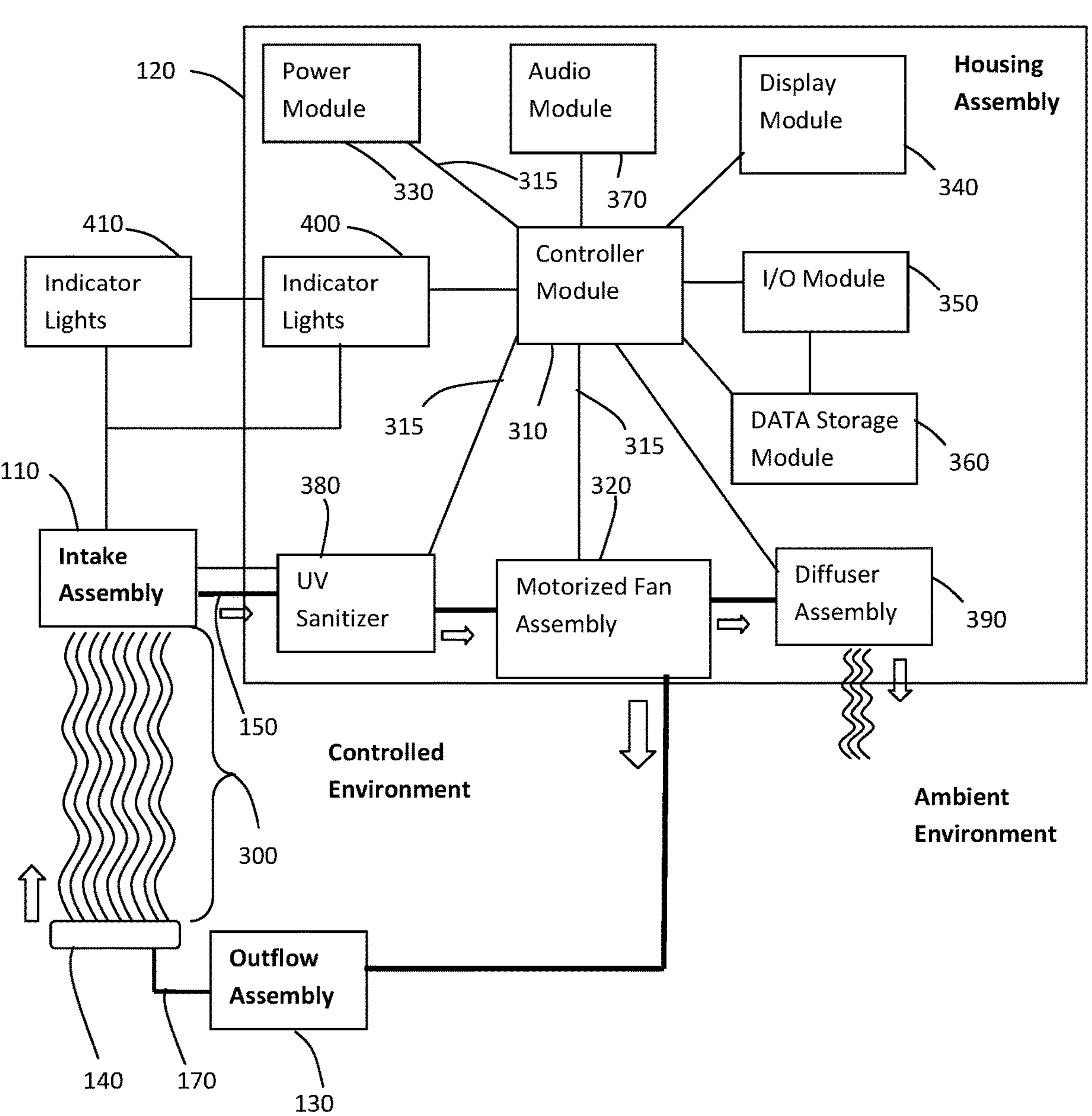
FIG. 4 is schematic diagram of the functional modules within the housing assembly in conjunction with the ducting for the in-take assembly and out-flow assembly of the air handling system.

FIG. 4 illustrates a schematic of the air flow of the system 100 and the functional components that may be included within housing assembly 120 to generate a controlled environment 300. The housing assembly 120 components include a controller module 310, a motorized fan assembly 320 and a power module 330. The housing assembly 120 may include other components or modules such as a display module 340, an input/output module 350 whereby the controller can wirelessly receive or send programs or machine data to or from external devices, a data storage module 360, an audio module 370, a UV sanitizer 380 and a diffuser assembly 390. The controller module 310 depicted is inclusive and may take the form of a computer system, programmable logic controller, microprocessor or combinations of the aforementioned. The controller module 310 is capable of controlling the motorized fan assembly 320 to provide air flow sufficient to create the desired air curtain and negative pressure environment to contain and diffuse any generated bioaerosols for filtration. Additionally, the controller can control the operation of the UV sanitizer 380 or the amount of air sent to the diffuser assembly 390 or bib 140 (manifold). Data on the number of auxiliary components in storage as well as the speed of the fan (and correlated air flow speed) can be wirelessly input to the controller module via the input/output module using known wireless protocols including Bluetooth and WIFI. Also located on the housing assembly are a speaker and a display as parts of the audio module 370 and display module 340. The speaker is used to provide audible feedback to the user during selection of a programmed operable mode for the controller and operation of the system. The display provides visual feedback for the fan operation as well as data relating to storage of auxiliary components and number of air room exchanges. The display is coupled to the controller module and is preferably a Thin Film Transistor liquid crystal display with touch screen capability however other types of display screens may be suitable. Together the first and second lights, speaker and display (as a part of their associated modules) form a user interface 180 that allows for the selection of a programmed operable mode for the controller, display of data during fan operation and providing feedback for any alarms. For instance, an alarm may be set to trigger when speed of the motorized fan is slower than it should be indicating a problem with the filter medium (i.e., filter is missing). When the alarm is triggered the user interface may provide feedback to the user in the form of alternating flashing of first and second lights, audible chirping through the speaker, flashing of the display or any combination thereof, informing the user to take some action.

Figure 5:
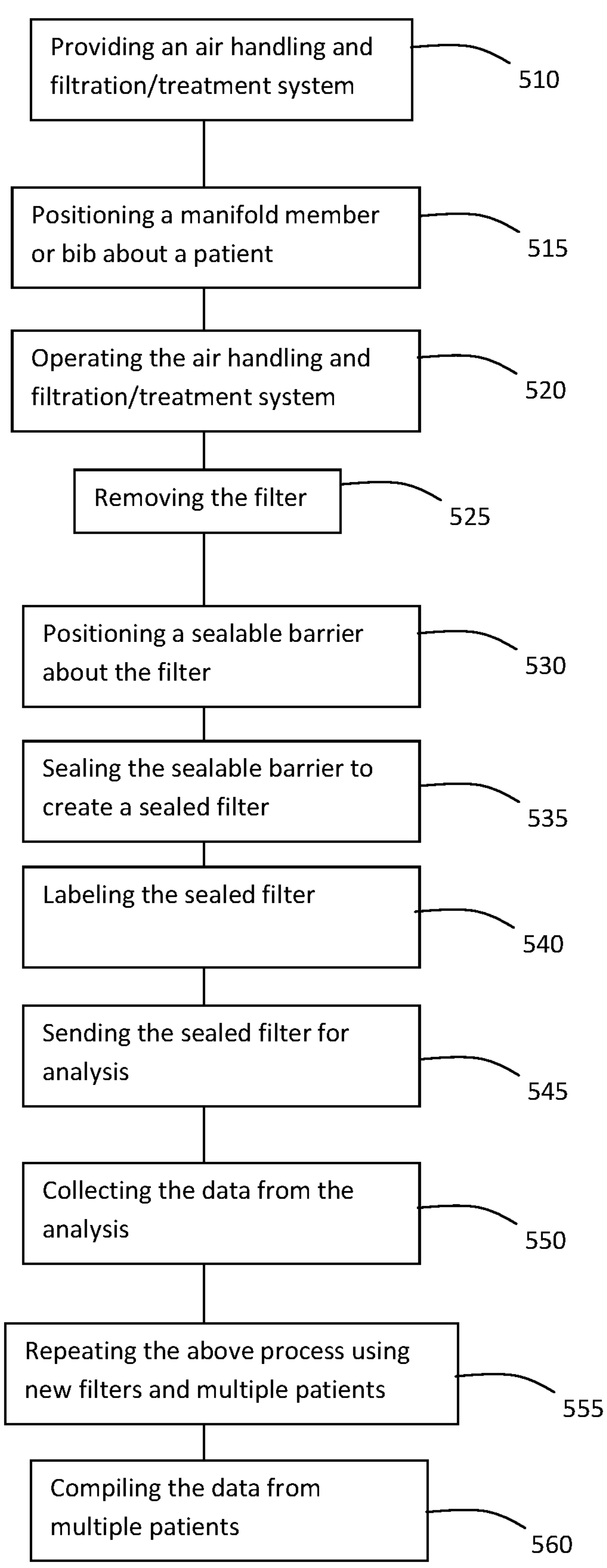
FIG. 5 is a chart illustrating method steps associated with preparing samples for pathogen analysis.

In addition to detailing an apparatus for air handling and filtration of bioaerosols generated from a patient there is also a non-invasive method of monitoring pathogens that may be generated within a population including those who may be asymptomatic. As depicted in FIG. 5, the method includes the steps of:

providing an air handling and filtration/treatment system according to the aforementioned system;

positioning the manifold or BIB member appropriately about a patient;

operating the air handling and filtration/treatment system such that bioaerosols generated from the patient are directed towards the filter by the airflow emanating from the orifices of the manifold or BIB member and subsequently captured within the filter;

removing the filter from the air handling and filtration/treatment system;

positioning a sealable barrier about the filter and or filter media (the sealable barrier may include suitable packaging materials such fluid tight rigid and or flexible containers or in the case of specialty designed filters the sealable barrier may constitute a non-permeable film that is attachable to a filter housing while covering the filter media creating a sealed filter configuration);

sealing said sealable barrier to create a sealed filter such that the filter and or filter media is not exposed to the ambient environment or other contaminants;

labeling the sealed filter with information that corresponds to procedural data that may include any of the following: patient ID, date, airflow settings, procedure type, procedure duration, time of procedure, temperature or humidity alone or in combination; and sending the sealed filter to a location so that the captured bioaerosols on the filter media can be analyzed to identify any potential pathogens.

The process of replacing a new filter in the air handling and filtration/treatment system with each new patient and the subsequent analysis of the filter for pathogens generates data that can be compiled to identify the general health of a population and or the spread of pathogens within a community. The collection and testing may be part of a national, state, or local health data system, or part of an integrated national, state, or local pathogen surveillance and forecasting system and act as a community-based early warning system, serving public health and biodefense.

FIG. 6 illustrates an embodiment of an air handling and filtration/treatment system 700 that includes a non-invasive diagnostic tool for real time or rapid detection and or identification of bioaerosols. The system 700 includes an intake assembly 710, a housing assembly 720, and an outflow assembly coupled to a bib 740 and may incorporate any of the aforementioned analogous components and modules of system 100, some of which are describe herein. Some of the components that may be included within housing assembly 720 to generate a controlled environment include a controller module 810, a motorized fan assembly 820 and a power module 830. The housing assembly 720 may include other components or modules such as a display module 840, an input/output module 850 whereby the controller can wirelessly receive or send programs or machine data to or from external devices, a data storage module 860, an audio module 870, a UV sanitizer 880 and a diffuser assembly 890. The controller module 810 depicted is inclusive and may take the form of a computer system, programmable logic controller, microprocessor or combinations of the aforementioned. The controller module 810 is capable of controlling the motorized fan assembly 820 to provide air flow sufficient to create the desired air curtain and negative pressure environment to contain and diffuse any generated bioaerosols for filtration. Additionally, the controller can control the operation of the UV sanitizer 880 or the amount of air sent to the diffuser assembly 890 or bib 740 (manifold). Data on the number of auxiliary components in storage as well as the speed of the fan (and correlated air flow speed) can be wirelessly input to the controller module via the input/output module using known wireless protocols including Bluetooth and WIFI. Also located on the housing assembly are a speaker and a display as parts of the audio module 870 and display module 840. Indicator lights 910 may be placed on the intake assembly to provide additional feedback to the system operator. Additionally, sensors 920 may be included in the system in various locations as needed to monitor room environmental properties including temperature, relative humidity, air sampling pH. The sensors 920 are preferably connected to the controller module 810 so that the data obtained may be initially captured. The information from the sensors may also be utilized in optimizing airflows in the controlled environment 800 based on the particular environmental conditions encountered.

A non-invasive diagnostic tool 930 may be incorporated into the intake assembly (preferably beneath the deflector or hood) in proximity to the removable filter. The diagnostic tool 930 may incorporate or utilize biosensors, chemical sensors, materials or reagents that change properties (e.g. color, shape, electrical, etc.) in the presence of pathogens, spectroscopy systems, microscopy systems or any combination of the aforementioned to aid in contaminate detection and or identification. The diagnostic tool may detect and or identify contaminants in the airflow directed towards the filter or captured on the filter. The data generated by the non-invasive diagnostic tool can be used to immediately trigger an alert (real time if necessary dependent upon the type of pathogen detected) and or be sent to the controller module to be captured along with data from other sensors and procedure data where it can be stored, processed, displayed and or transmitted to an external system. The external systems may include a centralized system for receiving data from multiple air handling and filtration treatment systems placed in various geographical locations to monitor pathogens in a community and or regional population.

There have been described and illustrated herein embodiments of an air handling and filtration/treatment system for mitigating and otherwise managing bioaerosols before, during, and after a dental procedure. While particular embodiments of the invention have been described, it is not intended that the invention be limited thereto, as it is intended that the invention be as broad in scope as the art will allow and that the specification be read likewise. It is specifically intended that aspects of the various embodiments can be combined with each other. It will therefore be appreciated by those skilled in the art that yet other modifications could be made to the provided invention without deviating from its scope as claimed.

What is claimed is:

1. An air handling and filtration/treatment system for use in performing dental procedures, comprising:

a) a housing assembly including a motorized fan assembly, a user interface and a controller;

b) an intake assembly including a removable filter, a first duct having a first end coupled to said housing assembly and a second end positioned laterally offset from said housing assembly, and a deflector positioned adjacent said second end, said first duct being in fluid communication with said fan assembly;

c) an outflow assembly including a second duct having a first end coupled to said housing assembly and a second end coupled to a manifold member, said manifold member being positioned vertically below said deflector and includes a plurality of orifices that direct airflow vertically towards the deflector, said second duct being in fluid communication with said fan assembly; and, said housing assembly further including an operable mode such that when said housing assembly is in said operable mode, operation of said motorized fan assembly causes the suction of air into said first duct second end and the expulsion of air through said second duct to thereby create a controlled environment positioned between said deflector and said manifold member whereby airflow emanating from said manifold is directed towards the deflector and is suctioned into said first duct second end.

2. The air handling and filtration/treatment system according to claim 1, wherein said removable filter is positioned at or near the terminable end of said first duct second end.

3. The air handling and filtration/treatment system according to claim 2, wherein said removable filter is a HEPA filter.

4. The air handling and filtration/treatment system according to claim 1, wherein said deflector is arcuate.

5. The air handling and filtration/treatment system according to claim 1, wherein said manifold member takes the form of a bib.

6. The air handling and filtration/treatment system according to claim 5, wherein said plurality of orifices are positioned adjacent the periphery of said bib.

7. The air handling and filtration/treatment system according to claim 5, wherein said bib is inflatable.

8. The air handling and filtration/treatment system according to claim 1, wherein said housing assembly includes a UV sanitizer.

9. The air handling and filtration/treatment system according to claim 1, wherein said intake assembly includes a UV sanitizer.

10. The air handling and filtration/treatment system according to claim 1, wherein said housing assembly includes a diffuser assembly such that when in said operable mode a portion of airflow from said fan assembly is directed to a diffuser member that reduces the air speed and discharges the air adjacent the housing assembly.

11. The air handling and filtration/treatment system according to claim 1, wherein said housing assembly includes a diffuser assembly such that when in said operable mode a portion of airflow from said fan assembly is directed to a diffuser member that reduces the air speed and discharges air to a manifold assembly.

12. The air handling and filtration/treatment system according to claim 1, wherein said airflow in said controlled environment is laminar.

13. The air handling and filtration/treatment system according to claim 1, wherein said airflow in said controlled environment has at least one speed of between 2 and 12 miles per hour.

14. The air handling and filtration/treatment system according to claim 1, wherein said intake assembly is telescoping.

15. The air handling and filtration/treatment system according to claim 1, wherein said intake assembly is vertically and horizontally adjustable.

16. A portable air handling and filtration/treatment system for use in performing dental procedures, comprising:

a) a housing assembly including a motorized fan assembly, a user interface and a controller;

b) an intake assembly including a removable filter, a first duct having a first end coupled to said housing assembly and a second end positioned laterally offset from said housing assembly, and a deflector positioned adjacent said second end, said first duct being in fluid communication with said fan assembly;

c) an outflow assembly including a second duct having a first end coupled to said housing assembly and a second end coupled to a manifold member, said manifold member being positioned opposite said deflector and includes a plurality of orifices that direct airflow towards the deflector, said second duct being in fluid communication with said fan assembly; and said housing assembly further including an operable mode such that when said housing assembly is in said operable mode, operation of said motorized fan assembly causes the suction of air into said first duct second end and the expulsion of air through said second duct to thereby define a controlled environment positioned between said deflector and said manifold member whereby airflow emanating from said manifold is directed towards the deflector and is suctioned into said first duct second end.

17. A method of monitoring bioaerosols generated from a patient comprising:

providing an air handling and filtration/treatment system according to claim 16;

positioning the manifold member appropriately about a patient;

operating the air handling and filtration/treatment system such that bioaerosols generated from the patient are directed towards the removable filter by the airflow emanating from the orifices of the manifold member and subsequently captured within the removable filter;

removing the removable filter from the air handling and filtration/treatment system;

positioning a sealable barrier about the removable filter;

sealing said sealable barrier such that the removable filter is not exposed to the ambient environment; and analyzing the sealed removable filter to determine captured bioaerosols.

18. The method according to claim 17 including labeling said sealable barrier with information that corresponds to procedural data.

* * * * *